United States Patent [19]

Prevo

[11] 4,392,450
[45] Jul. 12, 1983

[54] DEVICE FOR SPREADING MONOLAYERED FILMS

[76] Inventor: Donald L. Prevo, 907 Linden Ave., Winnetka, Ill. 60093

[21] Appl. No.: 348,209

[22] Filed: Feb. 12, 1982

Related U.S. Application Data

[63] Continuation-in-part of Ser. No. 234,011, Feb. 12, 1981, abandoned, which is a continuation-in-part of Ser. No. 185,020, Sep. 8, 1980, Pat. No. 4,359,013.

[51] Int. Cl.³ ............................................. B05C 17/10
[52] U.S. Cl. .................................. 118/120; 15/104 S; 118/401; 118/415
[58] Field of Search ............... 118/100, 120, 401, 415; 15/104 S; 427/2

[56] References Cited

U.S. PATENT DOCUMENTS

| | | | |
|---|---|---|---|
| 2,655,898 | 10/1953 | McNeil | 118/506 |
| 2,746,075 | 5/1956 | Gardner | 15/104 S |
| 3,683,850 | 8/1972 | Grabhorn | 118/100 |
| 3,880,111 | 4/1975 | Levine et al. | 118/100 X |
| 3,888,206 | 6/1975 | Faulkner | 118/100 |
| 4,030,341 | 6/1977 | Sullivan | 73/61.1 C |
| 4,151,915 | 5/1979 | Levine et al. | 206/456 |

FOREIGN PATENT DOCUMENTS

| | | |
|---|---|---|
| 830429 | 7/1938 | France . |
| 2315693 | 1/1977 | France . |

Primary Examiner—Evan K. Lawrence
Attorney, Agent, or Firm—McDougall, Hersh & Scott

[57] ABSTRACT

A spreader, movable over a base, coats a microscope slide or the like mounted on a supporting surface of the base with a single uniform layer of a fluid. The spreader comprises a support having legs for engaging the supporting surface, pressure pads for engaging the slide to hold the support above the slide having a fluid thereon, and a bar extending transversely along the lower surface of the support having a flat section and a cutaway section for uniformly spreading the fluid to create a monolayered film on the upper surface of the slide as the spreader is moved in a longitudinal direction along the length of the slide. The flat section and the cutaway section are maintain parallel to the slide and sloped surfaces extend upwardly in the longitudinal direction from the flat section and the cutaway section toward the support. Ramps are provided in tracks of the base to permit the bar to evenly disengage from contact with the film.

18 Claims, 8 Drawing Figures

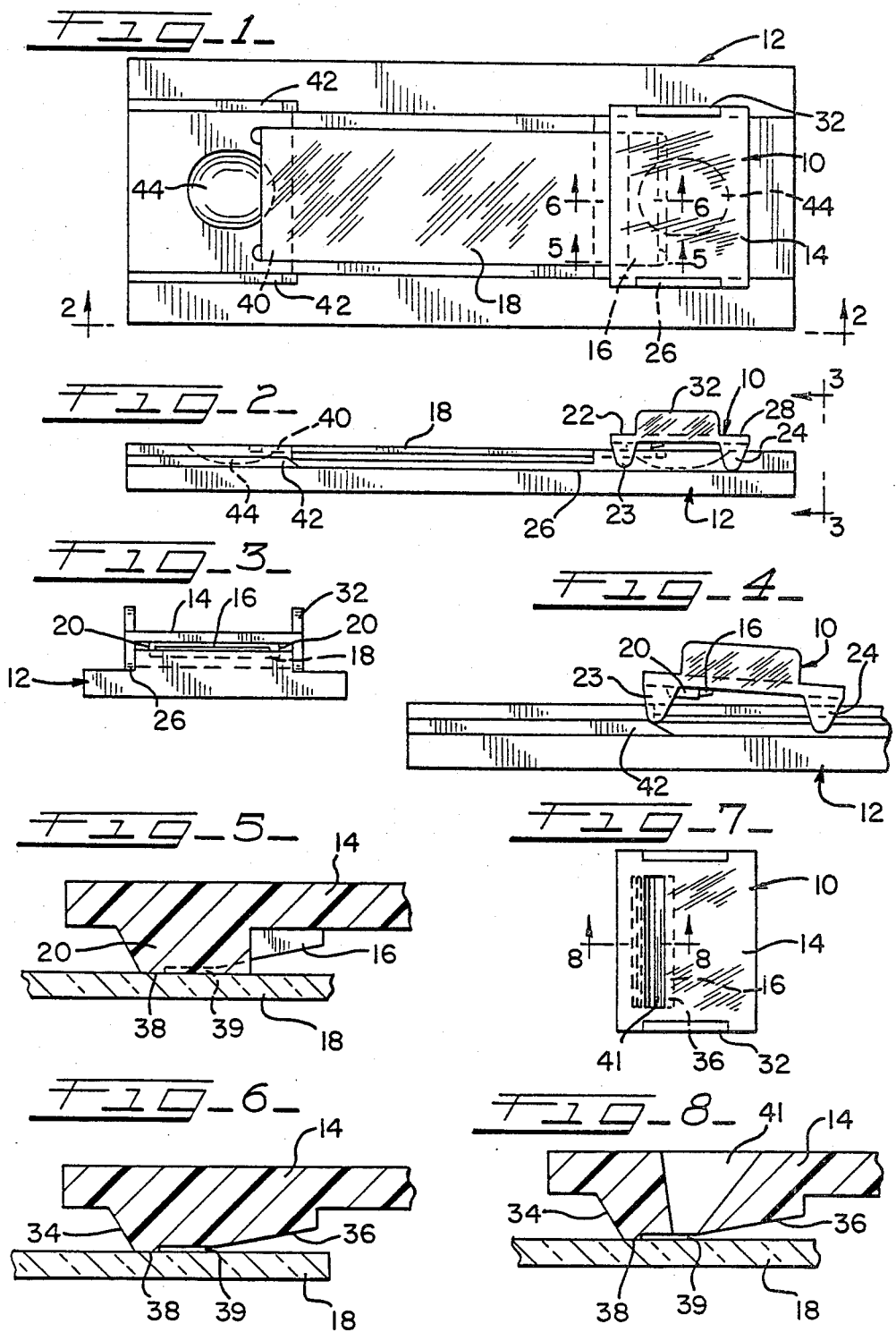

DEVICE FOR SPREADING MONOLAYERED FILMS

CROSS-REFERENCE TO RELATED APPLICATIONS

This application is a continuation-in-part of copending application Ser. No. 234,011, filed Feb. 12, 1981, abandoned, which is a continuation-in-part of copending application Ser. No. 185,020, filed Sept. 8, 1980, U.S. Pat. No. 4,359,013.

BACKGROUND OF THE INVENTION

The present invention relates generally to the preparation of monolayered films for use in the microscopic examination of fluids. In particular, the invention is a portable device for uniformly smearing a cellular fluid on a microscope slide or the like without substantially altering the morphology of the components in the fluid.

It is estimated that the medical profession performs between 500 and 600 million venipunctures annually. The drawn blood samples are routinely examined by microscopy so that individual cells can be observed and abnormal cells identified. The cells, when distributed in a single layer on a slide and treated with a stain, can be counted to provide an index with which to diagnose the condition of the patient.

An elementary method of preparing a slide film for microscopic examinaton is to place a small quantity of a fluid, such as blood, on a slide. If a thin sample layer is desired, a second slide is placed over the first so that the fluid is dispersed between the two slides by drawing the slides together. The drawing action of this manual smear technique can produce an inconsistent distribution of cells with considerable cell overlapping and render a cell count imprecise. Cells may also be mechanically stretched and deformed, thus making a proper evaluation of cell morphology difficult.

Alternatively, the second slide can be held at an angle with respect to the first slide and drawn across the upper surface of the latter. A constant angle between the slides must be maintained during the drawing motion; the angle is critical to the smearing of a uniform film, but such precision is difficult to attain. As a result, smears produced by this method are often streaked and unevenly distributed.

Rather than drawing the slides together, the slides can be centrifuged to evenly distribute the fluid. In this manner, the mechanical deformation of cells is minimized. Centrifugation, however, requires expensive equipment and once the centrifuge apparatus is positioned and balanced, it cannot be moved conveniently so the technique must be performed at a single location.

Thus, the need exists for a device for preparing a fluid sample for microscopic examination wherein a uniform distribution of cells is achieved and cell deformation is minimized. It is also advantageous to have an inexpensive, portable device. The present and the copending applications are directed to the fulfillment of these needs.

PRIOR ART STATEMENT

In accordance with the provisions of 37 CFR §1.97 et seq., the following references constitute the closest prior art of which applicant is aware:

U.S. Pat. No. 2,655,898 to McNeil relates to an apparatus for making blood films for microscopic examination. The apparatus comprises a support stand for aligning and retaining a slide, and a blade smearing implement for spreading a blood film across the slide. (See column 2, line 34—column 3, line 49 and FIGS. 1–3). The smearing implement, however, is hand-held and, like many other devices of the prior art, is difficult to maintain at the critical angle relative to the support stand or base that is necessary for spreading a monolayered film.

U.S. Pat. No. 3,683,850 to Grabhorn describes an apparatus for preparing blood specimens on slides having a test surface comprising guide means, a carrier mounted on the guide means for movement back and forth therealong, the carrier providing means for holding the slide to expose its test surface to receive a drop of blood at a predetermined spot thereon. A flexible, thin strip-like member extends toward the path of movement of the carrier to engage the test surface of the slide. Drive means moves the carrier at a predetermined speed in one direction along the guide means, the carrier being movable in the opposite direction along the guide means to the point at which a drop of blood on said spot just contacts and wets said member. (See column 6, lines 17–63 and FIGS. 3, 11–13.)

U.S. Pat. No. 3,880,111 to Levine et al. discloses an automatic device for preparing blood smears. A glass spreader is first pushed mechanically towards a drop of blood located at one end of a slide. After the spreader contacts the blood, a sufficient dwell time is allowed to permit the blood to diffuse along the lateral edges of the spreader. The spreader is then pulled in the reverse direction away from the blood sample at a predetermined speed. The method of operation is similar to that of the present invention. However, the device of the present invention is a simple, portable device that is operated manually. Levine et al. disclose a relatively complex, electrically operated device.

One major disadvantage of Levine et al. is the problem of motor vibration which can produce a chattering on the smear. U.S. Pat. No. 3,888,206 to Faulkner highlights this problem since Faulkner merely improves the aforementioned device of Levine et al. by adding a linkage assembly with shock absorbing means to dampen the vibrations and chatter which result during operation of the device.

U.S. Pat. 4,151,915 also to Levine et al. discloses another mechanical device for smearing a liquid on a slide. As with the previously described devices, the spreader is advanced to a predetermined point on the slide and then is retracted to its original position. The device is manually operated, but is still complex when compared to the construction and use of the present invention.

U.S. Pat. No. 4,030,341 to Sullivan discloses a hand-held device for applying small quantities of blood to a microscope slide. The device has a housing which includes a longitudinal aperture. At one end of the aperture a transverse groove is formed which intersects the aperture. Small quantities of blood from a capillary tube may be introduced into the longitudinal aperture and permitted to spread through the transverse groove so that a relatively thin and uniform layer of blood is deposited on a microscope slide by drawing the device across the microscope slide. (See column 2, lines 15–25 and FIGS. 1, 2 and 8.) Like the previously described hand-held devices, it is difficult to maintain the critical angle between slide and the device.

French patent application No. 2,315,693 and French Pat. No. 830,429 to Pinel apparently relate to the preparation of biological smears for microscopy and to a device for spreading blood, respectively. No translations are available.

None of these patents show, or even contemplate, a simple hand-held device that truly smears uniform monolayers of a fluid.

SUMMARY OF THE INVENTION

The invention is a device for depositing a uniform monolayer of a fluid on a planar surface, such as a slide, for use in the microscopic examination of the fluid. A base includes a supporting surface that holds the slide or the like on which is placed a small quantity of the fluid. A spreader comprising a support having legs removably positioned on the base and pressure pads in contact with the slide maintains the support above the slide. A bar on the lower surface of the support also is in contact with the upper surface of the slide so that when the spreader is pulled in one direction along the base and over the droplet, the fluid can diffuse within a cutaway section of the bar. The spreader is then moved in the opposite direction along the base and across the slide to uniformly smear the fluid by capillary action as a monolayer. Thus, there are two distinct motions of the spreader during the fluid spreading operation. The fluid can be dried to form a film which can be stained before analysis.

It is, therefore, the principal object of this invention to provide an improved device for the preparation of monolayered films. The films are uniform and suitable for use in microscopic analyses.

A further object of this invention is to provide a novel spreader for the preparation of monolayered films which is relatively economical and which can be disposed of after use, thereby avoiding any problems of contamination of specimens.

Other objects and advantages will be apparent from the following detailed description made with reference to the accompanying drawings.

BRIEF DESCRIPTION OF THE DRAWINGS

FIG. 1 is a top view of one embodiment of the invention;

Figure is a side view taken along the line 2—2 of FIG. 1;

FIG. 3 is an end view taken along line 3—3 of FIG. 2;

FIG. 4 is a partial side view of the invention illustrating the interaction of the spreader and the ramps of the base;

FIG. 5 is a sectional view taken along the line 5—5 of FIG. 1;

FIG. 6 is a sectional view taken along the line 6—6 of FIG. 1;

FIG. 7 is a top view of a second embodiment of the spreader; and

FIG. 8 is a sectional view taken along the line 8—8 of FIG. 7.

DETAILED DESCRIPTION

As illustrated in the drawings, the apparatus of the invention comprises a spreader 10 and a base, such as designated by reference numeral 12, which cooperates with the spreader. Both the spreader 10 and base 12 may be molded from a material of a kind that will flow when subjected to heat and pressure, and which is rigid when cooled, such as a thermoplastic. In addition, the base 12 can be constructed of any other durable material. The base is reusable, while the spreader is disposable. Use of the device of the invention permits the uniform application of any fluid monolayer on a microscope slide or the like. Because a new spreader is used for each coating operation, uniform fluid samples can be deposited without contamination by previously deposited samples.

The spreader 10 in the embodiment shown in FIGS. 5 and 6 comprises a support 14 and a bar 16 extending in a transverse direction across the bottom of the support for uniformly smearing the fluid monolayer on the upper surface of a microscope slide 18. The spreader 10 is maintained above the slide 18 by contact with the base 12 and the slide at five points. Specifically, the bar 16 rests on the upper surface of the slide to hold the front end 22 of the spreader over the slide (or the bar can be slightly spaced from the upper surface of the slide), and a set of rear legs 24 rests within tracks 26 on the base to hold the rear end 28 of the spreader in position. The front legs 23 do not rest on the base, as illustrated in FIG. 2, but simply serve to guide the front end 22 of the spreader and to prevent lateral movement of the spreader during the spreading motion. In addition, a pressure pad 20 located at each end of the bar 16 (see FIG. 3) rests on the upper surface of the slide to hold the front end 22 of the spreader at a predetermined distance above the slide. Handles 32 may be provided to facilitate gripping and moving the spreader 10 over the slide 18.

Referring again to FIGS. 5 and 6, the bar 16 includes sloped anterior and posterior surfaces 34 and 36, respectively. A flat section 38 and a cutaway section 39 are located between the sloped surfaces. When the spreader 10 is positioned above the top surface of the slide 18, the anterior sloped surface 34 of the bar 16 extends at an angle to the planar slide surface. In preferred embodiments, that angle is between 60° and 80° to the slide surface for the forming of whole blood films. The posterior sloped surface 36 of the bar 16 defines an angle of approximately 10° to 20° with respect to the aforesaid planar slide surface.

It will be understood that fluids in addition to blood, such as urine, mucus or a bacteria culture medium can be uniformly deposited on slides by the present invention, assuming appropriate dimensional changes are made in both the spacing between the top of the cutaway section 39 and the slide 18. For example, increasing the height of the cutaway section when spreading a red blood cell sample, decreases the space between cells. Decreasing the height of the cutaway section, on the other hand, disperses the sample and increases the space between cells. When a sample of whole blood is deposited, a gap of approximately 0.002 inch between the top of the cutaway section and the top surface of the slide has been found to produce an even distribution of blood cells. In addition, the flat section 38 and posterior sloped surface 36 of the bar 16 should be sufficiently smooth to insure an even contact between the cutaway section 39 and the fluid. An uneven contact could produce streaking of the sample and, in the case of a whole blood sample, considerable red blood cell overlapping. Fluids containing particulate matter or sediment also may be deposited as monolayers once the appropriate dimensional changes are made.

Referring again to FIG. 1, the base 12 securely holds within a recess 40 the slide 18 which is to be coated with the fluid. Tracks 26 on the base guide the front and rear legs 23 and 24, respectively, of the spreader 10 during the spreading operation. As best illustrated in FIG. 4, a ramp 42 at the end of each track 26, when in contact with the front legs 23, lifts the spreader 10 and thus the bar 16 from the proximity of the top surface of the slide 18 at the end of the drawing motion.

In the practice of this embodiment of the invention, a slide 18 is placed within the recess 40 of the base 12. A droplet of the fluid to be smeared is placed on the top surface of the slide 18 at the end of the slide opposite the ramps 42. The spreader 10 is then placed on the base 12 between the fluid droplet and the ramps 42 so that the front and rear legs 23 and 24 of the spreader ride in the tracks 26 of the base. With a continuous motion the spreader 10 is pulled slowly over the fluid droplet in a direction away from the ramps 42 so that the posterior sloped surface 36 and the cutaway section 39 of the bar move over the droplet and the fluid can diffuse by capillary action to fill the cutaway section with fluid. After a momentary pause to permit the fluid to diffuse within the cutaway section, the spreader is then pushed in the opposite direction toward the ramps 42 and across the slide 18. Thus, there are two distinct motions of the spreader during the fluid spreading operation.

The bar 16 and pressure pads 20, when in contact with the slide 18, maintain a fixed distance between the top of the cutaway section and the slide surface so that the cutaway section 39 does not contact the slide during the drawing motion. This fixed distance minimizes the possibility of shearing and deforming the cells. In addition, the flat section of the bar 16 (when in contact with the slide) and the pressure pads 20 produce drag or friction as the spreader 10 is moved over the slide to maintain the capillary action. The pressure pads 20, ensure a constant pressure between the spreader, the slide and the fluid within the cutaway section 39 and prevent compression of the bar during the drawing motion.

It should be noted that the spreader should be moved across the supporting surface with minimal downward pressure. If the bar is constructed so that the flat section contacts the surface of the slide when the slide is dry, as soon as the bar contacts the fluid, capillary spreading of the fluid will raise the spreader and movement of the spreader will form the monolayered film. The application of more than minimal downward pressure on the spreader during the spreading operation will tend to squeeze the fluid from between the flat section and the slide and produce a streaked or uneven film.

As the bar 16 reaches the end of the slide 18, the front legs 23 of the spreader 10 engage the ramps 42 within the tracks 26 to lift the bar 16 from the slide 18 and to break evenly the contact between the slide 18, fluid and bar 16. (See FIG. 4.) Alternatively, the spreader 10 may be lifted by the operator or by other means directly from the surface of the slide. Fingerholds 44 can be provided to allow the slide to be removed easily from the base 12 without deforming the flim.

As described, the fluid fills the cutaway section 39 and is advanced along the slide 18 during the spreading motion by the capillary action resulting from the proximity of the cutaway section 39 to the slide. Capillary action is a force that is the resultant of the adhesion, cohesion and surface tension in a liquid which is in contact with a solid, as in a capillary tube. When the cohesive force is greater, the surface of the liquid tends to rise or advance in the tube; when the adhesive force is greater, the liquid surface tends to be depressed in the tube. The cooperation of the flat section 38 with the bar 16 and pressure pads 20 which contact the slide produces the friction or drag and the downward pressure necessary to maintain the capillary action during the spreading motion.

A second embodiment of the spreader of the invention is shown in FIGS. 7 and 8. A slot 41 extends through the support 14 and the midsection of the bar 16 proximate to the posterior sloped surface 36 to join the top of the support and the top of the cutaway section 39. In addition, the slot 41 has an upper width greater than its lower width to form a funnel-shaped passage for receiving fluids. (See FIG. 8.) The slot can extend in a transverse direction across the support.

In the operation of this embodiment, a slide 18 is placed within the recess 40 of the base 12. The spreader 10 is placed on the base at the end opposite the ramps 42 so that the front and rear legs 23 and 24 of the spreader ride in the tracks 26 of the base. A quantity of fluid is then placed in the slot 41 of the spreader 10. The spreader is pulled slightly in a direction away from the ramps 42 across the slide 18 to allow the fluid to fill the cutaway section. Then with a continuous motion the spreader is pushed in the opposite direction toward the ramps 42 and across the slide, and the fluid is dispersed along the slide. As the bar 16 reaches the end of the slide 18, the front legs 23 of the spreader 10 engage the ramps 42 within the tracks 26, as previously described, to lift the bar 16 from the slide 18 and to break evenly the contact between the slide, fluid and bar. (See FIG. 4.)

This invention represents a sharp departure from conventional methods of forming fluid smears or films. A basic feature of the apparatus is the ability to hold and to distribute a fluid between two parallel planes as the spreader 10, which defines a first upper plane, is moved over the slide 18 forming a second, lower plane. In particular, the upper plane of the spreader comprises the top of the cutaway section 39 located on the bottom of the bar. This upper plane remains equidistant and parallel to the lower plane, the surface of the slide, during the movement of the spreader over the base 12.

A third plane, parallel to and below the two aforementioned planes, is defined by the tracks 26 of the base 12. The maintenance of this parallel configuration of the three planes and a constant distance between the top of the cutaway section 39 and the slide 18 is critical to the forming of unstreaked films having a uniform distribution of components. During the spreading operation, the bar 16 and, in particular, the pressure pads 20 move along the surface of the slide 18 and thus ensure parallelism between the cutaway section and the slide; while the rear legs 24 of the spreader move within the tracks 26 of the base 12 to ensure parallelism between the cutaway section and the base.

In addition, the cooperation of the cutaway section, the posterior sloped surface and the bar is essential to produce the capillary action necessary for forming a uniform, unstreaked film. The fluid is held under a given surface area defined by the cutaway section 39, while the constant posterior angle of the posterior sloped surface 36 releases the fluid at a constant rate to form the film.

The device has an additional advantage of being portable, and thus, it is capable of use at bedside in a hospital or clinic and in a doctor's office. The devices currently available for spreading monolayered blood films are too bulky for portable use. In fact, such devices seldom are removed from the laboratory. The procedure in most hospitals is to draw the blood sample from the patient, place the sample in a collection vial and take the sample to the laboratory for analysis. Use of the present device permits an immediate analysis of the blood by spreading a film at the time the blood is drawn.

This ability to spread the sample immediately after collection has several advantages. The intermediate step of placing the sample in a vial prior to analysis may be avoided. Collection vials may contain residual amounts of complexing agents or cleaning solutions which can contaminate the sample. For example, even small quantities of a complexing agent like disodium edetate (EDTA) can remove enough metal ions, including calcium and magnesium, from a red blood cell to distort the shape of the cell. Avoidance of this storage step prior to analysis of the sample prevents this possibility of a change in configuration.

In addition, the volume of blood needed for a microscopic analysis is decreased. Rather than drawing a volume of blood sufficient to fill the collection vial, only a droplet of blood is required. Therefore, the sample can be obtained merely by pricking the finger with a sharp instrument, placing the droplet directly on the slide and spreading immediately the droplet collected. This feature makes the device of the present invention particularly useful in pediatrics since infants have little blood to spare for frequent blood tests using a conventional method of smearing films.

It will be understood, of course, that various changes and modifications may be made in the above described apparatus without departing from the spirit thereof, particularly as defined in the following claims.

What is claimed to be new and is desired to be secured by Letters Patent is:

1. A spreader for forming a monolayered film on a slide or the like from a fluid placed on the slide, the spreader being movable in a longitudinal direction along the length of the slide, said slide being held by a supporting surface comprising:
   (a) a support having an upper surface and a lower surface;
   (b) a bar extending in a transverse direction and downwardly along said lower surface of said support, said bar including:
      (i) first and second sloped surfaces extending upwardly and in the longitudinal direction from the bottom of the bar toward said support, the first sloped surface comprising the forward end of the bar and the second sloped surface comprising the rear end of the bar;
      (ii) a flat section formed at an angle to the lower end of said first sloped surface such that said flat section engages said slide or the like; and
      (iii) a cutaway section adjacent to said flat section and formed at an angle to the lower end of said second sloped surface such that the top of said cutaway section is in close proximity with and is parallel to the slide on which the film is to be formed; and
   (c) means extending downwardly from either side of said cutaway section for maintaining the flat section in contact with a slide and the top of the cutaway section in close proximity with and parallel to the slide whereby as the spreader is placed over a droplet of fluid on the slide, the fluid can diffuse between the cutaway section and the slide so that the monolayered film can be formed as the spreader is moved in the forward direction over the slide.

2. A spreader as set forth in claim 1 including a slot that forms a passage connecting the upper surface of said support to the top of the cutaway section whereby a fluid placed within the slot can pass between the cutaway section and the slide so that the monolayered film can be formed as the spreader is moved over the slide.

3. A spreader as set forth in claim 1 wherein said bar includes a slot extending in said transverse direction and through said bar for receiving the fluid to be spread whereby as the spreader is moved over the slide the fluid flows by capillary action from the slot to the cutaway section and is deposited across the slide.

4. A spreader as set forth in claim 1, 2 or 3 wherein said means extending downwardly from either side of said cutaway section comprises pads mounted on each side of said bar and slightly below said cutaway section to engage the slide and to slightly space the top of said cutaway section parallel to the slide on which the monolayered film is to be formed.

5. A spreader as set forth in claim 1, 2 or 3 including at least one handle on the upper surface of said support for gripping the spreader to maintain a constant pressure between the spreader and a slide as the spreader is moved over the slide.

6. A spreader as set forth in claim 1, 2 or 3 further including means extending downwardly from either side of said support comprising legs for engaging the supporting surface when the slide is engaged by said means extending downwardly from either side of said cutaway section.

7. A spreader for forming a monolayered film on a slide or the like from a fluid placed on the slide, the spreader being movable in a longitudinal direction along the length of the slide, said slide being held by a supporting surface comprising:
   (a) a support having an upper surface and a lower surface;
   (b) a bar extending in a transverse direction and downwardly along said lower surface of said support, said bar including:
      (i) first and second sloped surfaces extending upwardly and in the longitudinal direction from the bottom of the bar toward said support, the first sloped surface comprising the forward end of the bar and the second sloped surface comprising the rear end of the bar;
      (ii) a flat section formed at an angle to the lower end of said first sloped surface; and
      (iii) a cutaway section adjacent to said flat section and formed at an angle to the lower end of said second sloped surface such that the top of said cutaway section is in close proximity with and is parallel to the slide on which the film is to be formed; and
   (c) means extending downwardly from either side of said cutaway section for maintaining the flat section and the top of the cutaway section in close proximity with and parallel to the slide whereby as the spreader is placed over a droplet of fluid on the slide, the fluid can diffuse between the cutaway section and the slide so that the monolayered film can be formed as the spreader is moved in the forward direction over the slide.

8. A spreader as set forth in claim 7 including a slot that forms a passage connecting the upper surface of said support to the top of the cutaway section whereby a fluid placed within the slot can pass between the cutaway section and the slide so that the monolayered film can be formed as the spreader is moved over the slide.

9. A spreader as set forth in claim 7 wherein said bar includes a slot extending in said transverse direction and through said bar for receiving the fluid to be spread whereby as the spreader is moved over the slide the fluid flows by capillary action from the slot to the cutaway section and is deposited across the slide.

10. A spreader as set forth in claim 7, 8 or 9 wherein said means extending downwardly from either side of said cutaway section comprises pads mounted on each side of said bar and slightly below said cutaway section to engage the slide and to slightly space the top of said cutaway section parallel to the slide on which the monolayered film is to be formed.

11. A spreader as set forth in claim 7, 8 or 9 including at least one handle on the upper surface of said support for gripping the spreader to maintain a constant pressure between the spreader and a slide as the spreader is moved over the slide.

12. A spreader as set forth in claim 7, 8 or 9 further including means extending downwardly from either side of said support comprising legs for engaging the supporting surface when the slide is engaged by said means extending downwardly from either side of said cutaway section.

13. A device for forming a monolayered film on a slide or the like from a fluid placed on the slide comprising a spreader and a base, the spreader being movable in a longitudinal direction along the length of the slide, said spreader including a support having an upper surface and a lower surface; a bar extending in a transverse direction and downwardly along said lower surface of said support, said bar including first and second sloped surfaces extending upwardly and in the longitudinal direction from the bottom of the bar toward said support, the first sloped surface comprising the forward end of the bar and the second sloped surface comprising the rear end of the bar, a flat section formed at an angle to the lower end of said first sloped surface such that said flat section engages said slide or the like, and a cutaway section adjacent to said flat section and formed at an angle to the lower end of said second sloped surface such that the top of said cutaway section is in close proximity with and is parallel to the slide on which the film is to be formed; first means extending downwardly from the lower surface of said support for maintaining the flat section in contact with the slide and the top of the cutaway section in close proximity with and parallel to the slide, and second means extending downwardly from the lower surface of said support having legs on either side of said support for engaging a base, said base comprising a supporting surface including a recess therein having parallel longitudinal sides for holding a slide in a stationary position; means on the supporting surface for guiding the legs of the spreader and preventing lateral movement of the spreader when the spreader is moved over a slide held within the recess; and a ramp at one end of said guiding means for receiving the legs of said spreader to lift the spreader from the supporting surface and disengaging evenly the bar from the contact with the film whereby as the spreader is placed over a droplet of fluid on the slide, the fluid can diffuse between the cutaway section and the slide so that the monolayered film can be formed as the spreader is moved in the forward direction over the base and the slide.

14. A device as set forth in claim 13 wherein said first means extending downwardly from the lower surface of said support comprises pads mounted on either side of said bar and slightly below said bar to engage said slide and to slightly space the flat section of said bar parallel to the slide on which the monolayered film is to be formed.

15. A device as set forth in claim 13 wherein said bar includes a slot extending transversely and through said bar for receiving a fluid to be spread whereby as the spreader is moved over said slide the fluid flows by capillary action from the slot to the cutaway section and is deposited across the slide.

16. A device for forming a monolayered film on a slide or the like from a fluid placed on the slide comprising a spreader and a base, the spreader being movable in a longitudinal direction along the length of the slide, said spreader including a support having an upper surface and a lower surface; a bar extending in a transverse direction and downwardly along said lower surface of said support, said bar including first and second sloped surfaces extending upwardly and in the longitudinal direction from the bottom of the bar toward said support, the first sloped surface comprising the forward end of the bar and the second sloped surface comprising the rear end of the bar, a flat section formed at an angle to the lower end of said first sloped surface, and a cutaway section adjacent to said flat section and formed at an angle to the lower end of said second sloped surface such that the top of said cutaway section is in close proximity with and is parallel to the slide on which the film is to be formed; first means extending downwardly from the lower surface of said support for maintaining the flat section and the top of the cutaway section in close proximity with and parallel to the slide; and second means extending downwardly from the lower surface of said support having legs on either side of said support for engaging a base, said base comprising a supporting surface including a recess therein having parallel longitudinal sides for holding a slide in a stationary position; means on the supporting surface for guiding the legs of the spreader and preventing lateral movement of the spreader when the spreader is moved over a slide held within the recess; and a ramp at one end of said guiding means for receiving the legs of said spreader to lift the spreader from the supporting surface and disengage evenly the bar from contact with the film whereby as the spreader is placed over a droplet of fluid on the side, the fluid can diffuse between the cutaway section and the slide so that the monolayered film can be formed as the spreader is moved in the forward direction over the base and the slide.

17. A device as set forth in claim 16 wherein said first means extending downwardly from the lower surface of said support comprises pads mounted on either side of said bar and slightly below said bar to engage said slide and to slightly space the flat section of said bar parallel to the slide on which the monolayered film is to be formed.

18. A device as set forth in claim 16 wherein said bar includes a slot extending transversely and through said bar for receiving a fluid to be spread whereby as the spreader is moved over said slide the fluid flows by capillary action from the slot to the cutaway section and is deposited across the slide.

* * * * *